US006530287B1

(12) United States Patent
Rodgers

(10) Patent No.: US 6,530,287 B1
(45) Date of Patent: Mar. 11, 2003

(54) ALPHA-ENVIRONMENTAL CONTINUOUS AIR MONITOR INLET

(75) Inventor: John C. Rodgers, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/930,348

(22) Filed: Aug. 15, 2001

(51) Int. Cl.$^7$ .................................................. G01N 5/00
(52) U.S. Cl. .................. 73/863.21; 73/28.04; 73/31.02; 73/864.81
(58) Field of Search ..................... 73/863.43, 863.33, 73/864.81, 28.04, 263.21, 31.02; 55/442

(56) References Cited

U.S. PATENT DOCUMENTS

| | | | |
|---|---|---|---|
| 4,461,183 A | * 7/1984 | Wedding | 73/863.21 |
| 4,942,774 A | 7/1990 | McFarland | 73/864.81 |
| 5,040,424 A | * 8/1991 | Marple et al. | 73/863.23 |
| 5,412,975 A | * 5/1995 | Raabe et al. | 73/28.04 |

* cited by examiner

Primary Examiner—Hezron Williams
Assistant Examiner—C D Garber
(74) Attorney, Agent, or Firm—Milton D. Wyrick

(57) ABSTRACT

A wind deceleration and protective shroud that provides representative samples of ambient aerosols to an environmental continuous air monitor (ECAM) has a cylindrical enclosure mounted to an input on the continuous air monitor, the cylindrical enclosure having shrouded nozzles located radially about its periphery. Ambient air flows, often along with rainwater flows into the nozzles in a sampling flow generated by a pump in the continuous air monitor. The sampling flow of air creates a cyclonic flow in the enclosure that flows up through the cylindrical enclosure until the flow of air reaches the top of the cylindrical enclosure and then is directed downward to the continuous air monitor. A sloped platform located inside the cylindrical enclosure supports the nozzles and causes any moisture entering through the nozzle to drain out through the nozzles.

7 Claims, 4 Drawing Sheets

*Fig. 3*

ALPHA-ENVIRONMENTAL CONTINUOUS AIR MONITOR INLET

Figure 1:
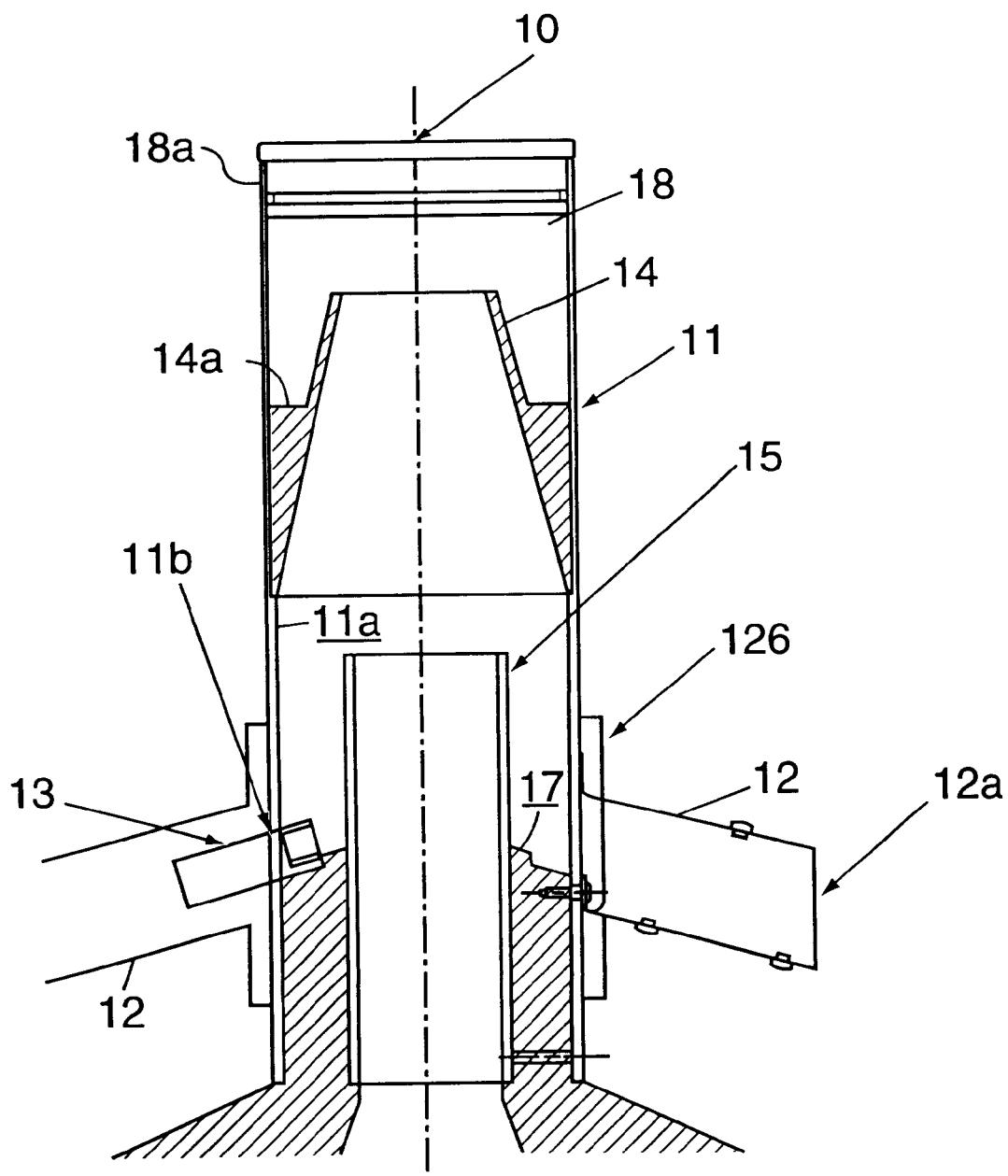
Figure 2:
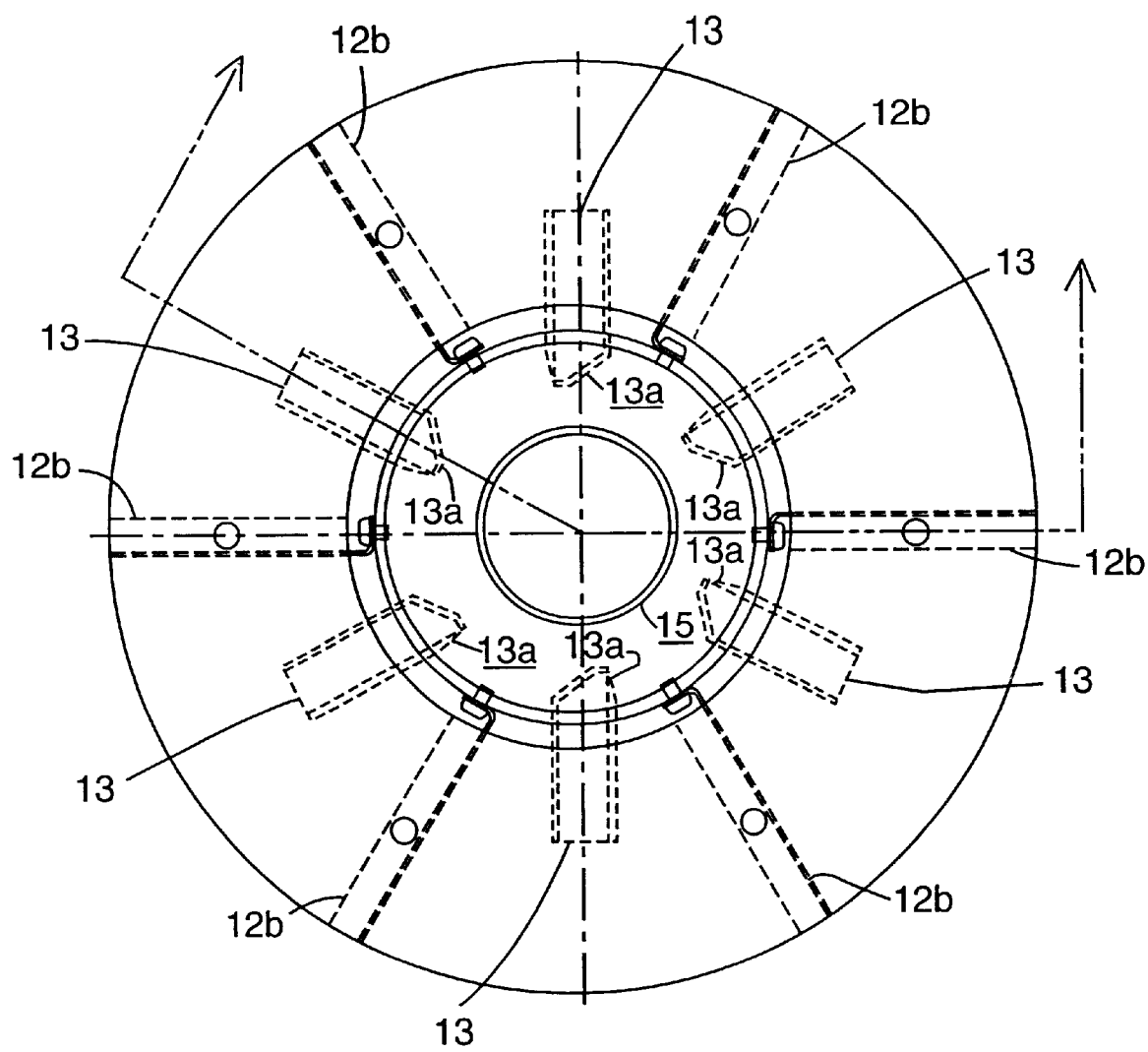
Figure 4:
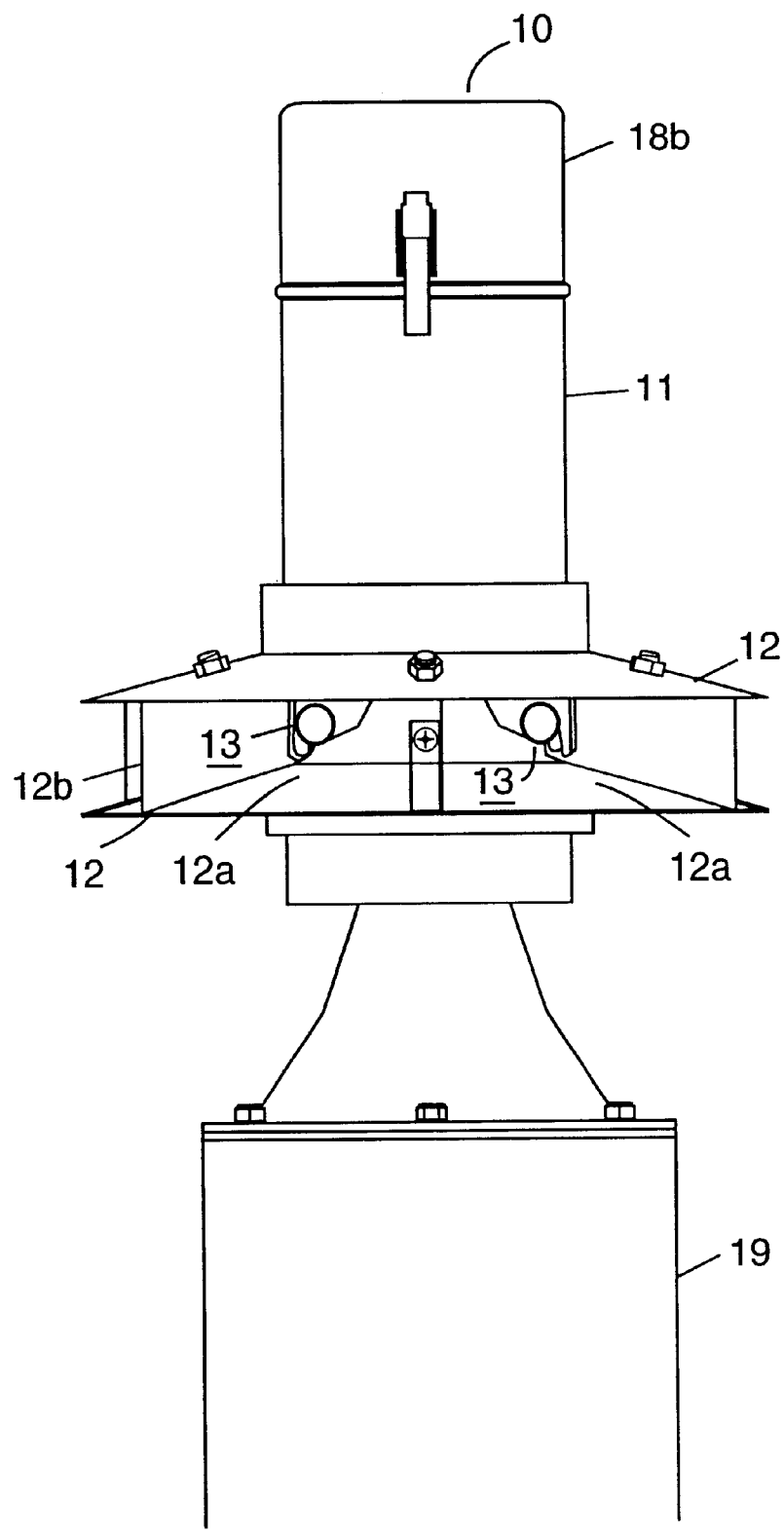

The present invention generally relates to continuous air monitors used for protection of individuals against radioactivity and, more specifically, to a continuous air monitor having shrouded inlets for interfacing between the ambient air and the input of the air monitor. This invention was made with Government support under Contract No. W-7405-ENG-36 awarded by the U.S. Department of Energy. The Government has certain rights in the invention.

BACKGROUND OF THE INVENTION

Although nuclear material accidents are rare, they do occur and safe handling of such accidents must be planned carefully. One of the more critical functions in this area is monitoring of an accident responder's exposure to airborne radioactivity resuspended in the air at the scene of a nuclear material accident. This is a difficult task, complicated by incomplete characterization of the location and distribution of the contaminants, adverse weather conditions, and accident sites that may be in remote areas.

Typically, air-sampling instruments deployed for assessing airborne radioactivity are classified as either high volume (HiVol) area samplers or personal breathing zone air (BZA) lapel samplers. Both of these types of air-sampling instruments usually require some form of laboratory analysis of their filters at the end of a sampling period, such as a day or a week. Often, analysis may be delayed for a period of time to allow for background decay. Although HiVol filter samples can be checked periodically in the field with handheld instruments to determine roughly the exposure conditions, the results are approximations, having poor sensitivity.

With these long sampling times and interruptions for background decay, there are significant and dangerous delays in assessing exposure conditions in field locations. As a result, accident responders may be put at risk should the contaminant situation suddenly change due to wind or other factors. In this situation, inadequately protected workers may not be relocated quickly, and engineering and administrative controls may not be used effectively. Alternatively, such conditions could cause workers to be placed into unnecessarily high levels of personal protective equipment (PPE) to assure protection.

As engineering controls may be of limited effectiveness under field conditions, and changes in exposure conditions may develop that are unknown to administrators, heavy reliance often is placed on the use of PPE to assure worker protection. However, the use of PPE has its limits, and associated hazards. For instance, it presents added stress to a worker's cardiovascular system from the respirator, and heat stress from the protective suit.

These situations can be avoided through use of existing Environmental Continuous Air Monitors (ECAM) having inlets equipped with the present invention. Administrators and managers at the accident site will know about any airborne hazards from frequent (30 or fewer minutes) updates. By combining the radiological and accident meteorological data from an ECAM with the present invention in place and plutonium resuspension forecasting, the conditions likely to be found in the nearby downwind direction also can be brought into administrative and management decisions as they evolve.

U.S. Pat. No. 4,942,774, issued Jul. 24, 1990, to McFarland, for "Anisokinetic Shrouded Aerosol Sampling Probe" discloses a shrouded probe involving a nozzle having a narrowed diameter end inside a cylindrical shroud. The aerosols captured in the nozzle are input directly into a filter sampler or a continuous air monitor. The present invention differs in significant respects from U.S. Pat. No. 4,942,774, as will hereinafter be made clear.

One of the challenges presented in a field accident location is providing accurate radiation analysis under windy and rainy conditions. The present invention provides a shrouded inlet that smoothes the transition from the ambient wind to the inlet velocity for the ECAM, and that protects the inlet from rain or other precipitation. It further provides particle size selection to exclude large particle components.

It is therefore an object of the present invention to provide a particle size-selected shrouded inlet for an environmental continuous air monitor that smoothes the transition from ambient wind velocity to the proper air velocity for the inlet of the monitor and contemporaneously minimizes the wall losses of aerosol particles in the inlets.

It is another object of the present invention to provide a shrouded inlet that minimizes the entry of rain and other precipitation into the inlet of the continuous air monitor and onto its sample filter.

It is still another object of the present invention to provide a shrouded inlet that removes large particle components in the sampled air by a cyclonic flow of air before such particles reach the sample filter of a continuous air monitor.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, a wind deceleration and protective shroud for providing representative samples of ambient aerosols to a continuous air monitor (CAM) comprises a cylindrical enclosure having a first end and a second end, the second end being mounted to an input on the continuous air monitor, the cylindrical enclosure defining at least three apertures located radially about its periphery. At least three nozzles having first and second ends, having their first end extending into the cylindrical enclosure through each of the at least three apertures and their second end open to receive ambient air flows direct the air flows upward through said cylindrical enclosure. A sloped platform located inside the cylindrical enclosure supports the first end of the at least three nozzles and causes any moisture entering through the at least three nozzles to drain out through the at least three nozzles; wherein the flow of air creates a cyclonic flow up through the cylindrical enclosure until the flow of air reaches the first end of the cylindrical enclosure and is directed downward to the continuous air monitor.

In another aspect of the present invention and in accordance with its objects and principles, a method of sampling the particulates in a flowing stream of ambient air comprises the steps of decelerating the flowing stream of ambient air; removing a representative sample of particles entrained in the flowing stream of ambient air; creating a cyclonic flow of the representative sample of particles thereby removing any large particle component of the representative sample of particles, leaving a PM-10 inspirable component to be analyzed; and analyzing the PM-10 inspirable component to determine characteristics of any inspirable particulates in the PM-10 inspirable component.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1 is a cross-sectional front view of one embodiment of the present invention.

FIG. 2 is a schematic representation of a cyclonic flow established by a nozzle according to the present invention.

Figure 3:
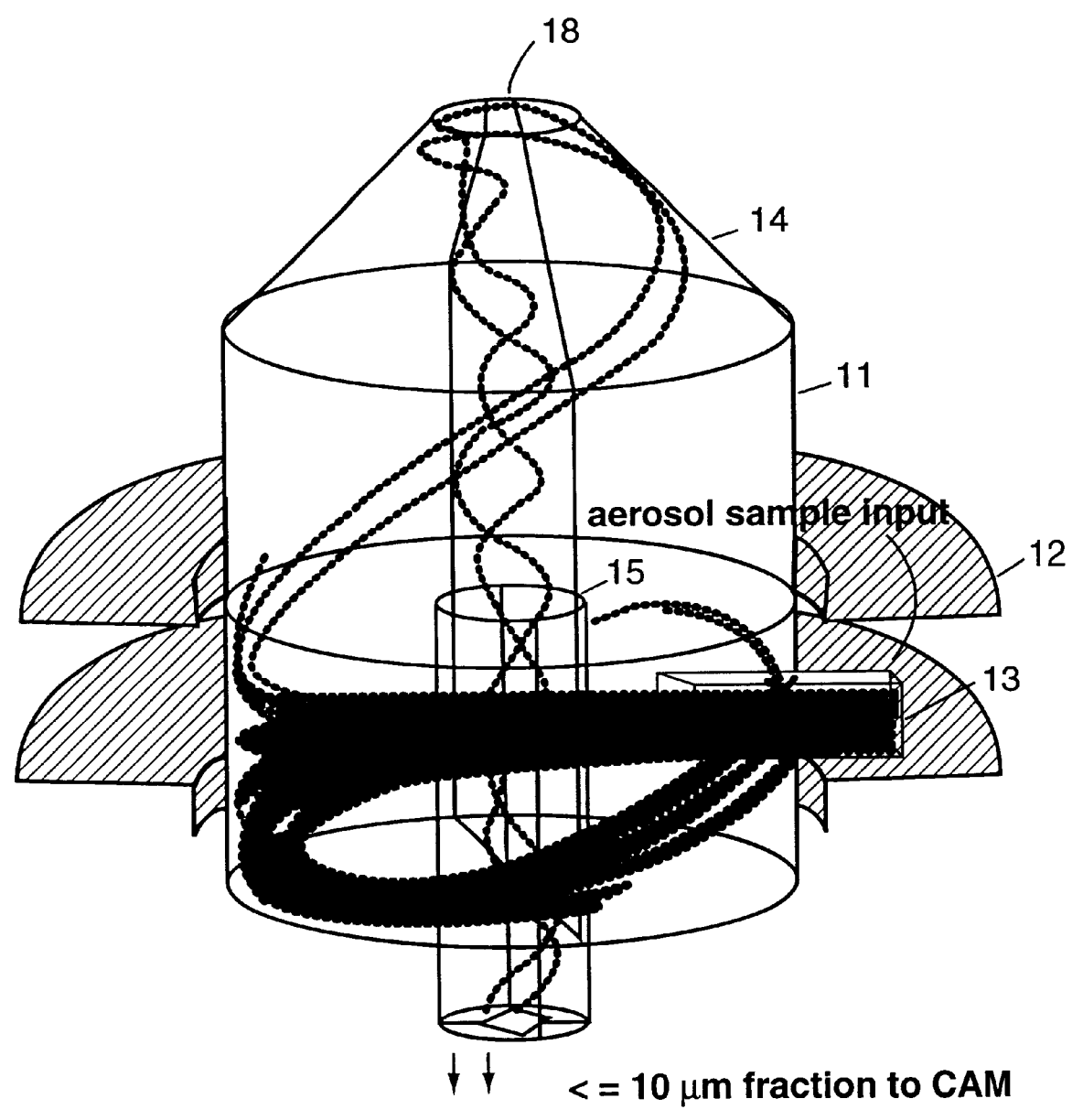

FIG. 3 is a cross-sectional top view of one embodiment of the present invention.

FIG. 4 is a plan view of an embodiment of the present invention attached to a continuous air monitor.

DETAILED DESCRIPTION

The present invention provides an effective omni-directional shrouded nozzle ambient aerosol-sampling inlet for an Environmental Continuous Air Monitor (ECAM). The invention can be most easily understood through reference to the drawings.

In FIG. 1, there can be seen a cross-sectional side view of one embodiment of the present invention where cyclo-shroud 10 defines outer enclosure 11 and attached wind decelerators 12. Wind decelerators 12 decelerate the wind and direct wind currents either into nozzles 13 or out through apertures 11*b* between wind channels 12 and outer enclosure 11. In this embodiment, six wind decelerators 12, spaced radially at equal separations are used. However, three or more wind decelerators 12 can be used for particular applications. In the present invention, therefore, an omni-directional array of shrouded inlet nozzles can be achieved with a shared air pump (not shown) in an associated ECAM (not shown), and with shared bypass flow around outer enclosure 11. These features are among those that distinguish the present invention, and represent a departure from the unitary shrouded probe nozzle concepts of the prior art.

Ambient wind carrying a broad spectrum of dust particles, some of which may be radioactive in certain environments, entering nozzles 13, being a representative sample of the ambient aerosol, is induced, with the flow of air created by the negative pressure of an air pump associated with an attached continuous air monitor, into an upwardly moving circular path against interior surface 11*a* of outer enclosure 11 by nozzles 13. As the induced air flow travels up interior surface 11*a* in cyclonic flow, it encounters a gradually reduced volume created by conical deflector 14, thereby increasing the velocity of the cyclonic flow. As this flow of cyclone air exits conical deflector 14, it enters an expansion area of outer enclosure 11 where it continues to swirl but is pulled downward by and through the low pressure inside the cyclonic flow. The downward flowing air flows into outlet cylinder 15 and on into an attached ECAM (see FIG. 4) where the aerosols in the air flow are filtered by a sample filter for analysis.

Should water be blown into cyclo-shroud 10 through nozzles 13, it will be collected on shelf 17. As seen, shelf 17 is sloped and nozzles 13 fit into notch 17*a* of conical deflector. With this arrangement, any collected water is returned out of nozzles 13 when allowed to do so by a lower flow of air into nozzles 13.

As a part of this invention, outlet cylinder 15 is properly dimensioned with respect to the size of outer enclosure 11 so that larger particles in the airflow are excluded from the sample filter of an attached continuous air monitor. It has been determined that a pump in the associated continuous air monitor producing an air flow through the inlet of approximately 4 cfm assists in this process. In this case, by the cyclone separation of the larger particle size fraction of the ambient aerosol sample, only the inspirable fraction (sometimes referred to as the PM-10 sample) of $D_{50}=10\ \mu m$ is delivered to the sample filter of the attached continuous air monitor.

The method by which this cyclonic flow of air is established can be understood from reference to FIG. 2. Here, a top view of wind decelerators 12 is shown in cross-section. For illustration purposes only, six (6) decelerator sections 12*a* are illustrated. For specific application, any number of decelerator sections 12*a* can be used. Each decelerator section 12*a* has segregating walls 12*b* and a nozzle 13 located in aperture 11*b*. As shown, each nozzle 13 has deflector caps 13*a,* which are configured so as to direct air passing there through in a clockwise and slightly upward direction against interior surface 11*a* of outer enclosure 11. This termination of nozzles 13 by deflector caps 13*a,* which is another distinguishing characteristic of the present invention that distinguishes it over the unitary shrouded probe of the prior art whose nozzle does not terminate in a cap of any kind.

The movement of air inside outer enclosure 11 is depicted in FIG. 3. Here, it can be seen that air entering through nozzles 13 is directed upward along interior surface 11*a* of outer enclosure 11 by deflector caps 13*a*. Deflector caps 13*a* have an opening to the right side of nozzles 13 that is tilted slightly upward in order to create a cyclonic flow of the air to be sampled. This cyclonic flow of air spirals around and upward along interior surface 11*a*.

Returning to FIG. 1, as the air encounters conical deflector 14, the cyclone diameter is narrowed causing the flow to be accelerated, and the centrifugal forces on large particles in the air are increased. When the flow of air reaches top section 18 of outer enclosure 11 and encounters top cap 18*a,* where the air is deflected down through the center of the cyclonic flow of air and into input cylinder 15, large particles impact to the side-walls of outer enclosure 11 and thus are removed to flat trap 14*a* of conical deflector 14.

The air then passes into the body of an ECAM (not shown) where aerosol particles are collected on a filter, which is viewed continuously by a solid-state radiation detector. Any suitable detector may be used, including those to detect alpha, gamma or beta radiation.

Referring now to FIG. 4, a plan view of cyclo-shroud 10 according to the present invention is shown mounted onto ECAM 19. As shown, top cap 18*a* conveniently may be made to be detachable for cleaning of flat trap 14*a* (FIG. 1). This figure illustrates the efficient manner in which cyclo-shroud 10 is secured to ECAM 19 for field applications.

The various components of cyclo-shroud 10 may be made of any appropriate material. In one exemplary embodiment, all the components are made of spun or machined stainless steel. If desired, and appropriate for the application, the components also could be made of plastic or any other useful material. Combinations of materials also could be used.

The foregoing description of the embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A wind deceleration and protective shroud that provides representative samples of ambient aerosols to an environmental continuous air monitor (ECAM) comprising:

a cylindrical enclosure having a first end and a second end, said second end being mounted to an input on said ECAM, said cylindrical enclosure defining at least three apertures located radially about its periphery;

at least three nozzles having first and second ends, said first end extending into said cylindrical enclosure through each of said at least three aperture and said second end open to receive ambient air flows and direct said air flows upward through said cylindrical enclosure;

a sloped platform located inside said cylindrical enclosure supporting said first end of said at least three nozzles and causing any moisture entering through said at least three nozzles to drain out through said at three one nozzles;

wherein said flow of air creates a cyclonic flow up through said cylindrical enclosure until said flow of air reaches said first end of said cylindrical enclosure and is directed downward to said input of said ECAM.

2. The wind deceleration and protective shroud as described in claim 1 further comprising a conically shaped deflector in said cylindrical enclosure and spaced apart from said first end of said cylindrically shaped enclosure for narrowing said flow of air to accelerate said flow of air, said conical deflector including a flat trap for collecting large particles from said flow of air.

3. The wind deceleration and protective shroud as described in claim 1 further comprising a wind decelerator mounted to said cylindrical enclosure in a manner to allow an outlet for wind between said at least one wind decelerator and said cylindrical enclosure, for decelerating wind entering said at least one nozzle.

4. The wind deceleration and protective shroud as described in claim 1 wherein said first end of each said at least three nozzles is effective to direct wind against said cylindrical enclosure so that said wind spirals around said cylindrical enclosure moving toward said first end of said cylindrical enclosure.

5. The wind deceleration and protective shroud as described in claim 1 wherein said first end of said cylindrical enclosure is detachable.

6. The wind deceleration and protective shroud as described in claim 1 wherein said at least three nozzles comprises three nozzles.

7. The wind deceleration and protective shroud as described in claim 1 wherein said at least three nozzles comprises six nozzles.

* * * * *